US009089536B2

(12) United States Patent
Smith

(10) Patent No.: US 9,089,536 B2
(45) Date of Patent: Jul. 28, 2015

(54) OPHTHALMIC SOLUTION FOR ABSORBING ULTRAVIOLET RADIATION AND METHOD FOR ABSORBING ULTRAVIOLET RADIATION

(76) Inventor: Brian J. Smith, Irvine, CA (US)

(*) Notice: Subject to any disclaimer, the term of this patent is extended or adjusted under 35 U.S.C. 154(b) by 52 days.

(21) Appl. No.: 13/489,561

(22) Filed: Jun. 6, 2012

(65) Prior Publication Data

US 2013/0331362 A1    Dec. 12, 2013

(51) Int. Cl.

| | | |
|---|---|---|
| *A61K 31/4184* | (2006.01) | |
| *A61K 31/525* | (2006.01) | |
| *A61K 31/618* | (2006.01) | |
| *A61K 31/277* | (2006.01) | |
| *A61K 31/216* | (2006.01) | |
| *A61K 45/06* | (2006.01) | |
| *A61K 9/00* | (2006.01) | |
| *A61K 31/12* | (2006.01) | |
| *A61K 31/675* | (2006.01) | |
| *A61K 47/10* | (2006.01) | |
| *A61K 47/26* | (2006.01) | |

(52) U.S. Cl.
CPC ............ *A61K 31/216* (2013.01); *A61K 9/0048* (2013.01); *A61K 31/12* (2013.01); *A61K 31/277* (2013.01); *A61K 31/4184* (2013.01); *A61K 31/618* (2013.01); *A61K 31/675* (2013.01); *A61K 45/06* (2013.01); *A61K 47/10* (2013.01); *A61K 47/26* (2013.01)

(58) Field of Classification Search
USPC .................................. 514/163, 251, 394, 521
See application file for complete search history.

(56) References Cited

U.S. PATENT DOCUMENTS

| | | |
|---|---|---|
| 4,765,977 A | 8/1988 | Baron |
| 4,788,007 A | 11/1988 | Baron |
| 5,041,244 A | 8/1991 | Baron |
| 5,503,825 A | 4/1996 | Lane |
| 6,106,849 A | 8/2000 | Malkan |
| 6,143,387 A | 11/2000 | Kubler |
| 6,146,618 A | 11/2000 | Bell |
| 6,475,500 B2 | 11/2002 | Vatter |
| 6,669,951 B2 | 12/2003 | Rothbard |
| 6,890,912 B2 | 5/2005 | Lyles |
| 6,919,473 B2 | 7/2005 | Bonda |
| 7,097,828 B2 | 8/2006 | Meyer |
| 7,666,442 B2 | 2/2010 | Morariu |
| 7,776,915 B2 | 8/2010 | Morariu |
| 7,910,090 B2 | 3/2011 | Dueva-Koganov |
| 2007/0059258 A1 | 3/2007 | Chaudhuri |
| 2007/0160547 A1 | 7/2007 | Duffy |
| 2008/0286217 A1 | 11/2008 | Chaudhuri |
| 2008/0318833 A1 | 12/2008 | Jermann |
| 2009/0068255 A1* | 3/2009 | Yu et al. ........................ 424/450 |
| 2009/0130035 A1 | 5/2009 | Lange |
| 2010/0040566 A1 | 2/2010 | Faiyaziannasab |
| 2010/0111884 A1 | 5/2010 | Acker |
| 2010/0143272 A1 | 6/2010 | Muller |
| 2010/0305209 A1 | 12/2010 | Theberge |

OTHER PUBLICATIONS

Daxer, A., Blumthaler, M., Schreder, J., Ettl, A., Effectiveness of Eye Drops Protective Against Ultraviolet Radiation, Ophthalmic Res. 1998; 30(5); 286-90, http://www.ncbi.nlm.nih.gov/pubmed/9704331.
Krasnovidov, VS, Lysak, VF, Osopovich, VK, Protection of the Human Skin and Eyes Against Solar UV-Radiation, Kosm Biol Aviakosm Med., Jul.-Aug. 1991; 25(4):43-6, http://www.ncbi.nlm.nih.gov/pubmed/1960954.
Feldman, Brad H., M.D., Corneal Collagen Cross-Linking, EyeWiki, http://eyewiki.aao.org/Corneal_Collagen_Cross-Linking.
Dykas, How to Protect Patients From Harmful Sunlight, 20/20 Magazine, Jun. 2004, pp. 1-3, http://www2020mag.com/ce/TTViewTest.aspx?LessonID=3127.

* cited by examiner

*Primary Examiner* — Zohreh Fay
(74) *Attorney, Agent, or Firm* — Hinshaw & Culbertson LLP

(57) ABSTRACT

An ophthalmic solution is provided. The ophthalmic solution includes an ultraviolet-A absorber and an ultraviolet-B absorber. The ophthalmic solution has a viscosity of between about 1 and 100 cps. The ophthalmic solution can be used to absorb ultraviolet radiation in the eye.

16 Claims, No Drawings

OPHTHALMIC SOLUTION FOR ABSORBING ULTRAVIOLET RADIATION AND METHOD FOR ABSORBING ULTRAVIOLET RADIATION

FIELD OF THE INVENTION

The present invention relates to an ophthalmic solution including an ultraviolet-A (UV-A) radiation absorber and an ultraviolet-B (UV-B) radiation absorber. The ophthalmic solution can be used to absorb UV-A and UV-B radiation that comes in contact with an eye. The present invention also relates to a method for absorbing UV-A and UV-B radiation that comes in contact with an eye.

BACKGROUND OF THE INVENTION

Exposure to ultraviolet radiation can cause aging of cells and mutagenic changes to cells within the human body. Solar ultraviolet radiation is present in the rays of the sun, resulting in repeated and regular exposure by an eye to UV-A and UV-B radiation. The human ocular system does not develop a tolerance to repeated ultraviolet exposure.

The acute effects of repeated and regular UV-A and UV-B radiation exposure include conjunctivitis and photokeratitis, a corneal inflammation reaction. Exposure to UV-A and UV-B radiation also contributes to early formation of cataracts, especially in persons with blonde hair and blue eyes living in sun belt zones of the United States.

It is important for the cornea to have an optically smooth surface for the formation of a sharp visual image on the retina. Repeated exposure to ultraviolet radiation can result in the swelling or shrinking of groups of corneal epithelial cells. This can lead to visibly recognizable stippling or irregular mosaic granulation of the corneal surface. With UV-A and UV-B exposure greater than the threshold for photokeratitis, surface epithelial cells exhibit nuclear fragmentation, mid-epithelial cells exhibit vacuole formation, and basal cells exhibit inhibition of mitosis and clouding of the corneal stroma occurs.

A healthy cornea prevents exposure by the retina to ultraviolet radiation. When the cornea is damaged or replaced, the eye becomes extremely sensitive to ultraviolet radiation and the retina is exposed to ultraviolet radiation.

The retina is a delicate nervous membrane upon which the images of external objects are received. A healthy retina is soft, semitransparent, and has a purple tint. Upon exposure to ultraviolet radiation it becomes clouded, opaque, and bleached. Prolonged exposure to ultraviolet radiation causes damage to the retina.

High-energy visible light (HEV light) is high-frequency light in the violet/blue band in the visible spectrum, between 380 and 500 nm. HEV light is thought to be a cause of age-related macular degeneration resulting from damage to the central portion of the retina. Although it has not been conclusively shown to cause retinal damage, absorption of HEV light has been shown to cause a reversal in the natural visual cycle, resulting in a greater potential for oxidative damage to the eye. Thus, the lens of the eye and the retina may show irreversible changes induced by prolonged exposure to moderate levels of HEV light. Additionally, following an intraocular lens implant, the retina becomes particularly sensitive to HEV light exposure.

A need exists for an ophthalmic solution that can be applied to the eye to absorb ultraviolet radiation and to filter out HEV light.

BRIEF SUMMARY OF THE INVENTION

The present invention provides ophthalmic solutions and packaged ophthalmic solutions for absorbing UV-A and UV-B radiation and filtering out HEV light. In addition, methods of absorbing ultraviolet radiation, such as UV-A and UV-B radiation, and filtering HEV light using ophthalmic solutions are provided.

In one aspect of the invention, an ophthalmic solution is provided. In particular, the ophthalmic solution comprises a UV-A absorber and a UV-B absorber and has a viscosity of between about 1 and 100 cps. The ophthalmic solution may have a pH of between about 6.4 and 8.4.

In one embodiment, the UV-A absorber is avobenzone and the UV-B absorber is ethylhexyl methoxycinnamate.

In another embodiment, the viscosity of the ophthalmic solution is between about 4 and 12 cps. In another particular embodiment, the viscosity of the ophthalmic solution is about 8 cps.

In another aspect of the invention, the ophthalmic solution contains homosalate, an additional UV-A absorber.

In another aspect of the invention, the ophthalmic solution contains octisalate, an additional UV-A absorber.

In another aspect of the invention, the ophthalmic solution contains octocrylene, an additional UV-A absorber.

In another aspect of the invention, the ophthalmic solution contains oxybenzone, an additional UV-A absorber.

In another aspect of the invention, the ophthalmic solution contains ensulizole, an additional UV-B absorber.

In another embodiment, the ophthalmic solution further comprises at least one preservative, at least one surfactant, at least one buffering agent to maintain a desired pH, a viscosity building agent, and at least one emulsifier.

In an additional embodiment, an ophthalmic solution is provided. The ophthalmic solution comprises between about 0.05 and 0.6% by weight avobenzone; between about 0.05 and 0.6% by weight ethylhexyl methoxycinnamate; between about 1 and 5% by weight polysorbate 80; between about 1 and 5% by weight propylene glycol; between about 0.01 and 0.1% by weight methyl paraben; and between about 0.009 and 0.1% by weight propyl paraben. The ophthalmic solution has a viscosity between about 1 and 100 cps and a pH between about 6.4 and 8.4.

In another embodiment, the ophthalmic solution further comprises between about 0.05 and 1% by weight of at least one adjuvant or additional UV-A absorber selected from the group consisting of homosalate, octisalate, octocrylene, and oxybenzone.

In an additional embodiment, the ophthalmic solution further comprises between about 0.05 and 1% by weight ensulizole.

In another embodiment, the ophthalmic solution further comprises an HEV filter. In a particular embodiment, the ophthalmic solution contains between about 0.01 and 2.66 µM riboflavin-5-sodium phosphate.

In another embodiment, a method of absorbing UV-A and UV-B radiation contacting the eye is provided. The method comprises providing an ophthalmic solution comprising an ultraviolet-A absorber and an ultraviolet-B absorber, and applying the ophthalmic solution to an eye. The ophthalmic solution has a viscosity of between about 1 and 100 cps. A suitable viscosity building agent may be utilized. Suitable viscosity building agents can be selected from cetyl alcohol, polysorbate 80, propylene glycol and methyl cellulose, for example.

In a further embodiment, the ophthalmic solution also comprises riboflavin-5-sodium phosphate. The riboflavin-5- sodium phosphate indicates when the ophthalmic solution needs to be reapplied to the eye.

In one particular embodiment, the UV-A absorber is avobenzone. In another particular embodiment, the UV-B absorber is ethylhexyl methoxycinnamate.

In a further embodiment, the ophthalmic solution further comprises at least one additional UV-A absorber, selected from the group comprising homosalate, octisalate, octocrylene, and oxybenzone.

In another embodiment, the ophthalmic solution further comprises an additional UV-B absorber, ensulizole.

In another particular embodiment, the ophthalmic solution has a viscosity of about 8 cps and a pH of between about 6.4 and 8.4.

DETAILED DESCRIPTION OF THE INVENTION

The present invention is directed to an aqueous dispersion of at least one chromophore to form an ophthalmic solution to absorb UV-A and UV-B radiation and filter out HEV light in the eye.

The ophthalmic solution of this invention can be used to absorb UV-A and UV-B radiation and filter out HEV light in the eye. The visible light spectrum of light is around 400 nm and above. UV-A radiation has a wavelength of between about 325 nm and 400 nm. UV-B radiation has a wavelength of between about 290 nm and 325 nm.

A typical UV-A absorber for use in the ophthalmic solution of the present invention is avobenzone. Avobenzone has the molecular formula:

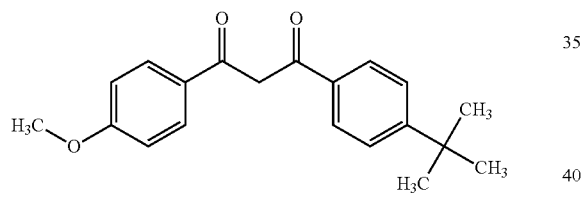

Avobenzone absorbs ultraviolet light over a wide range of wavelengths, absorbing up to a maximum of 357 nm.

The present invention typically contains a chromophore to absorb UV-B radiation. A typical UV-B absorber for use in the ophthalmic solution of the present invention is ethylhexyl methoxycinnamate. Ethylhexyl methoxycinnamate has the molecular formula:

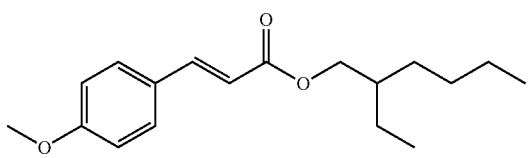 [SMILES: CCCCC(CC)COC(=O)/C=C/c1ccc(OC)cc1]

Ethylhexyl methoxycinnamate is an oil soluble, essentially colorless, and essentially odorless liquid. Ethylhexyl methoxycinnamate is an effective UV-B absorber, and use of ethylhexyl methoxycinnamate in an ophthalmic solution will absorb UV-B radiation, resulting in less UV-B radiation reaching and affecting the cornea and retina.

The ophthalmic solution typically has a viscosity of between about 1 and 100 cps. More typically, the ophthalmic solution has a viscosity of between about 1 and 25 cps. More typically, the ophthalmic solution has a viscosity of between about 4 and 12 cps. Most typically, the ophthalmic solution has a viscosity of about 8 cps.

Optionally, a suitable viscosity building agent may be utilized. Suitable viscosity building agents can be selected from cetyl alcohol, polysorbate 80, propylene glycol and methyl cellulose, for example. A viscosity building agent may not be needed to reach the desired viscosity, but may be desired to maintain retention of the eye drop.

The present invention can contain any suitable chromophore to absorb ultraviolet radiation. Examples of chromophores that can be used in the ophthalmic solution include, but are not limited to, avobenzone, ethylhexyl methoxycinnamate, homosalate, octisalate, octocrylene, oxybenzone, and ensulizole. The ophthalmic solution may contain any of the listed chromophores in any combination, or may contain any suitable chromophore for instilling onto the human eye and that effectively absorbs ultraviolet radiation. The chromophore may be present in any suitable amount to absorb ultraviolet radiation when instilled onto the exterior surface of the human eye.

The ophthalmic solution can include homosalate. Homosalate absorbs ultraviolet rays with a wavelength from about 295 nm to about 315 nm and has the molecular formula:

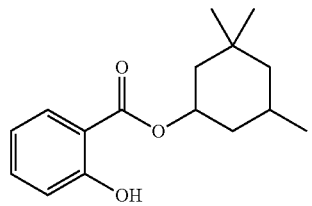 [SMILES: CC1CC(OC(=O)c2ccccc2O)CC(C)(C)C1]

The ophthalmic solution can also include octisalate. Octisalate absorbs ultraviolet rays, particularly UV-B radiation, and has the molecular formula:

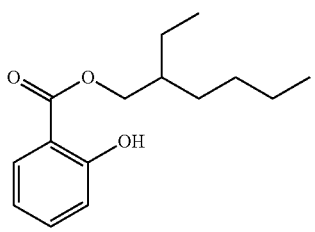 [SMILES: CCCCC(CC)COC(=O)c1ccccc1O]

The ophthalmic solution can also include octocrylene. Octocrylene absorbs ultraviolet rays with a wavelength between about 280 nm to about 320 nm and has the molecular formula:

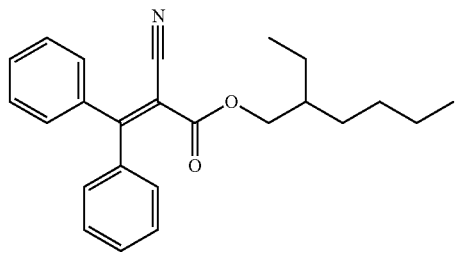 [SMILES: CCCCC(CC)COC(=O)C(C#N)=C(c1ccccc1)c1ccccc1]

The ophthalmic solution can also include oxybenzone. Oxybenzone absorbs both UV-A and UV-B radiation, with an absorption spectrum extending to less than about 350 nm. Oxybenzone is colorless crystals that readily dissolve in most organic solvents and has the molecular formula:

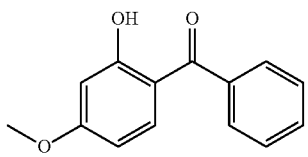 [SMILES: COc1ccc(C(=O)c2ccccc2)c(O)c1]

The ophthalmic solution can also include ensulizole. Ensulizole absorbs primarily UV-B radiation, is water soluble, and has the molecular formula:

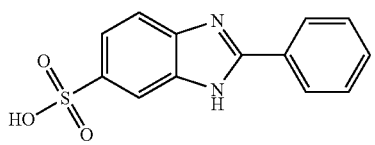 [SMILES: O=S(=O)(O)c1ccc2nc(-c3ccccc3)[nH]c2c1]

The ophthalmic solution can also include an HEV filter. Typically, a yellow dye is utilized as an HEV filter. Any ophthalmically appropriate yellow dye may be utilized. Typically, riboflavin, in the form of riboflavin-5-sodium phosphate, is utilized as an HEV filter. The yellow dye also serves to indicate when it is necessary to reapply the ophthalmic solution. Typically, the ophthalmic solution comprises between about 0.01 and 2.66 µM riboflavin-5-sodium phosphate. The ophthalmic solution comprises between about 0.2 and 1.5 µM riboflavin-5-sodium phosphate.

Inactive ingredients in the ophthalmic solution include polysorbate 80, propylene glycol, methyl paraben, and propyl paraben. Any other inactive ingredients may be added as necessary.

The balance of the ophthalmic solution is purified water, and the solution is adjusted to a pH of between about 6.4 and 8.4 using 0.1 N NaOH. Typically, the solution has a pH of about 7.4.

The ophthalmic solution is typically isotonic. The ophthalmic solution is typically a micelle suspension.

Typically, the ophthalmic solution comprises between about 0.05% and 1% by weight avobenzone. The ophthalmic solution can comprise between about 0.2% and 0.5% by weight avobenzone. Alternatively, the ophthalmic solution can comprise between about 0.05% and 0.2% by weight avobenzone. In one specific embodiment, the ophthalmic solution comprises about 0.1% by weight avobenzone.

Typically, the ophthalmic solution comprises between about 0.05% and 1% by weight ethylhexyl methoxycinnamate. The ophthalmic solution can comprise between about 0.2% and 0.5% by weight ethylhexyl methoxycinnamate. Alternatively, the ophthalmic solution can comprise between about 0.05% and 0.2% by weight ethylhexyl methoxycinnamate. In one specific embodiment, the ophthalmic solution comprises about 0.1% by weight ethylhexyl methoxycinnamate.

The ophthalmic solution may comprise homosalate. Typically, the ophthalmic solution comprises between about 0.05% and 1% by weight homosalate. The ophthalmic solution can comprise between about 0.2% and 0.5% by weight homosalate. Alternatively, the ophthalmic solution can comprise between about 0.05% and 0.2% by weight homosalate. In one specific embodiment, the ophthalmic solution comprises about 0.1% by weight homosalate.

The ophthalmic solution may comprise octisalate. Typically, the ophthalmic solution comprises between about 0.05% and 1% by weight octisalate. The ophthalmic solution can comprise between about 0.2% and 0.5% by weight octisalate. Alternatively, the ophthalmic solution can comprise between about 0.05% and 0.2% by weight octisalate. In one specific embodiment, the ophthalmic solution comprises about 0.1% by weight octisalate.

The ophthalmic solution may comprise octocrylene. Typically, the ophthalmic solution comprises between about 0.05% and 1% by weight octocrylene. The ophthalmic solution can comprise between about 0.2% and 0.5% by weight octocrylene. Alternatively, the ophthalmic solution can comprise between about 0.05% and 0.2% by weight octocrylene. In one specific embodiment, the ophthalmic solution comprises about 0.1% by weight octocrylene.

The ophthalmic solution may comprise oxybenzone. Typically, the ophthalmic solution comprises between about 0.05% and 1% by weight oxybenzone. The ophthalmic solution can comprise between about 0.2% and 0.5% by weight oxybenzone. Alternatively, the ophthalmic solution can comprise between about 0.05% and 0.2% by weight oxybenzone. In one specific embodiment, the ophthalmic solution comprises about 0.1% by weight oxybenzone.

The ophthalmic solution may comprise ensulizole. Typically, the ophthalmic solution comprises between about 0.05% and 1% by weight ensulizole. The ophthalmic solution can comprise between about 0.2% and 0.5% by weight ensulizole. Alternatively, the ophthalmic solution can comprise between about 0.05% and 0.2% by weight ensulizole. In one specific embodiment, the ophthalmic solution comprises about 0.1% by weight ensulizole.

The ophthalmic solution of the invention may also include one or more surfactant(s) and emulsifier(s). The surfactant(s) and emulsifier(s) function to maintain dispersion of the lipophilic components. Suitable surfactants and emulsifiers may be selected from nonionic surfactants, cationic surfactants, polysorbates, hydroxypropyl methyl cellulose, benzalkonium chloride, and combinations thereof. Examples of nonionic surfactants and emulsifiers include polysorbates such as polysorbate 80, glyceryl esters, polyoxyethylene glycol esters and ethers, and the sorbitan fatty acid esters and their polyoxyethylene derivatives. Polysorbate 80 is a nonionic surfactant and emulsifier that can form part of the ophthalmic solution of the present invention. Typically, the ophthalmic solution comprises between about 1% and 5% by weight polysorbate 80. More typically, the ophthalmic solution comprises between about 1% and 3% by weight polysorbate 80. Most typically, the ophthalmic solution comprises about 2% by weight polysorbate 80.

Propylene glycol is a colorless and nearly odorless viscous liquid with many different uses. Propylene glycol is utilized as a solvent in pharmaceuticals, as an emulsification agent, and as a moisturizer. Typically, the ophthalmic solution comprises between about 1% and 5% by weight propylene glycol. More typically, the ophthalmic solution comprises between about 1% and 3% by weight propylene glycol. Most typically, the ophthalmic solution comprises about 2% by weight propylene glycol.

The ophthalmic solution may contain a variety of preservatives as appropriate to provide a stable solution and prohibit microbial and fungal growth. Preservatives are typically present when the ophthalmic solution is packaged in multi-dose containers. A preservative is not typically needed when the ophthalmic solution is packaged in a monodose container.

Examples of preservatives that can be found in the ophthalmic solution include, but is not limited to, methyl paraben, propyl paraben, benzalkonium chloride, benzethonium chloride, cetyl pyridinium, benzyl bromide, EDTA, phenylmercury nitrate, phenylmercury acetate, thimerosal, merthiolate, acetate and phenylmercury borate, polymyxin B sulphate, chlorhexidine, methyl and propyl parabens, phenylethyl alcohol, quaternary ammonium chloride, sodium benzoate, sodium propionate and sorbic acid. The ophthalmic solution may contain any effective amount of a preservative or combination of preservatives necessary to provide a stable solution and prohibit microbial and fungal growth.

Typically, the ophthalmic solution may contain methyl paraben and/or propyl paraben in any effective amount for prohibiting microbial and fungal growth without detrimentally affecting the ophthalmic solution. The ophthalmic solution may also be stored in single-use vials which do not require the use of a preservative.

Methyl paraben is an antimicrobial and anti-fungal agent that is considered generally recognized as safe (GRAS) for food, pharmaceutical, and cosmetic antibacterial preservation. Typically, the ophthalmic solution comprises between about 0.01% and 0.1% by weight methyl paraben. More typically, the ophthalmic solution comprises between about 0.025% and 0.075% by weight methyl paraben. Most typically, the ophthalmic solution comprises about 0.05% by weight methyl paraben.

Propyl paraben is an antimicrobial and anti-fungal agent that is considered GRAS for food, pharmaceutical, and cosmetic antibacterial preservation. Typically, the ophthalmic solution comprises between about 0.001% and 0.1% by weight propyl paraben. More typically, the ophthalmic solution comprises between about 0.009% and 0.075% by weight propyl paraben. Most typically, the ophthalmic solution comprises about 0.01% by weight propyl paraben.

The ophthalmic solution typically has a viscosity of between about 1 and 100 cps. The low viscosity of the ophthalmic solution allows the solution to easily form a drop that can be applied directly into an eye. Typically, the ophthalmic solution has a viscosity between about 2 and 25 cps. Typically, the ophthalmic solution has a viscosity between about 4 and 12 cps. More typically, the ophthalmic solution has a viscosity of about 8 cps.

The ophthalmic solution typically has a pH of between about 6.4 and 8.4. Typically, the ophthalmic solution has a pH of between about 7.2 and 7.6. Most typically, the ophthalmic solution has a pH of about 7.4.

An ophthalmic solution in accordance with the invention can be packaged in any suitable container known to those skilled in the art. Any type of packaging and packaging material that is suitable for storing the ophthalmic solution of the invention may be utilized. Non-limiting examples of packaging include bottles, ampules, pouches and envelopes. The packaging material generally should exhibit a high degree of oxygen and other gas impermeability. For that reason, pouches and envelopes could be made of a foil laminate material as is well known in the art. The packaging typically will be suitable for allowing the ophthalmic solution to be instilled directly into the eye in a drop-wise fashion. A squeeze bottle or an eye drop bottle may be utilized, for example.

The ophthalmic solution is topically administered to the eye or eye area about every three to six hours or as needed for protection from HEV light and UV-A and UV-B radiation.

Alternatively, the ophthalmic solution is topically administered to the eye or eye area as often as indicated by a yellow visibility marker.

Another aspect of the present invention relates to a method of absorbing UV-A and UV-B radiation contacting the eye. The method of ultraviolet radiation contacting the eye comprises topically administering to an eye an ophthalmic solution as described herein. An ophthalmic solution as described herein is provided. The ophthalmic solution comprises an UV-A absorber and an UV-B absorber, wherein the ophthalmic solution has a viscosity of between about 1 and 100 cps. The ophthalmic solution may have a viscosity of between about 4 and 12 cps and a pH between about 6.4 and 8.4. Typically, the ophthalmic solution comprises between about 0.05% and 0.6% by weight avobenzone; between about 0.05% and 0.6% by weight ethylhexyl methoxycinnamate; between about 1% and 5% by weight polysorbate 80; between about 1% and 5% by weight propylene glycol; between about 0.01% and 0.1% by weight methyl paraben; and between about 0.001% and 0.1% by weight propyl paraben. The ophthalmic solution is topically administered to the eye.

The method may also filter HEV light. An ophthalmic solution as described herein is provided. The ophthalmic solution includes an HEV filter, such as riboflavin-5-sodium phosphate. Riboflavin-5-sodium phosphate also serves as a yellow visibility marker. The yellow visibility marker indicates when the ophthalmic solution needs to be topically reapplied to the eye.

The ophthalmic solution may also contain other ultraviolet absorbers, such as but not limited to, homosalate, octisalate, octocrylene, oxybenzone, and/or ensulizole.

EXAMPLES

The present invention is described in more detail with reference to the following non-limiting examples, which are offered to more fully illustrate the invention, but are not to be construed as limiting the scope thereof.

Example 1

An ophthalmic solution with the following formulation can be prepared:

TABLE 1

| Compound | Weight Percent (%) |
| --- | --- |
| Avobenzone | 0.1% |
| Ethylhexyl methoxycinnamate | 0.1% |
| Polysorbate 80 | 2% |
| Propylene glycol | 2% |
| Methyl paraben | 0.05% |
| Propyl paraben | 0.01% |
| Purified water | q.s. |
| 0.1N NaOH | Adjust to a pH of 7.4 |

Example 2

The ophthalmic solution of Example 1 can be topically administered to a patient to absorb UV-A and UV-B radiation in the eye. The ophthalmic solution can be topically administered directly on the eye at least daily.

While the invention has been described with respect to certain preferred embodiments, as will be appreciated by those skilled in the art, it is to be understood that the invention is capable of numerous changes, modifications and rearrangements, and such changes, modifications and rearrangements are intended to be covered by the following claims.

What is claimed is:

1. An ophthalmic solution for absorbing ultraviolet radiation when applied to a person's eye comprising an ultraviolet-A absorber selected from the group consisting of avobenzone and oxybenzone, and an ultraviolet-B absorber selected from the group consisting of ethylhexyl methoxycinnamate, homosalate, octisalate, octocrylene, and ensulizole, wherein the ophthalmic solution has a viscosity of between about 1 and 100 cps, the composition is suitable for ophthalmic use on a person's eye and when applied on a person's eye the composition is capable of absorbing ultraviolet-A and ultraviolet-B radiation.

2. The ophthalmic solution of claim 1 wherein the ultraviolet-A absorber is avobenzone and the ultraviolet-B absorber is ethylhexyl methoxycinnamate.

3. The ophthalmic solution of claim 1 wherein the ophthalmic solution has a pH of between about 6.4 and 8.4 and has a viscosity between about 4 and 12 cps.

4. The ophthalmic solution of claim 3 wherein the viscosity is about 8 cps.

5. The ophthalmic solution of claim 2 further comprising homosalate.

6. The ophthalmic solution of claim 2 further comprising octisalate.

7. The ophthalmic solution of claim 2 further comprising octocrylene.

8. The ophthalmic solution of claim 2 further comprising oxybenzone.

9. The ophthalmic solution of claim 2 further comprising ensulizole.

10. The ophthalmic solution of claim 1 further comprising an HEV filter, the composition capable of absorbing high-energy visible light when applied to a person's eye.

11. The ophthalmic solution of claim 10 wherein the HEV filter is riboflavin-5-sodium phosphate.

12. An ophthalmic solution for absorbing ultraviolet and high-energy visible radiation when applied on a person's eye comprising:
  between about 0.05% and 0.6% by weight avobenzone;
  between about 0.05% and 0.6% by weight ethylhexyl methoxycinnamate;
  between about 1% and 5% by weight polysorbate 80;
  between about 1% and 5% by weight propylene glycol;
  between about 0.01% and 0.1% by weight methyl paraben; and
  between about 0.009% and 0.1% by weight propyl paraben;
wherein the ophthalmic solution has a viscosity between about 1 and 100 cps and a pH between about 6.4 and 8.4, the composition is suitable for ophthalmic use on a person's eye and when applied on a person's eye the composition is capable of absorbing ultraviolet and high-energy visible radiation.

13. The ophthalmic solution of claim 12 further comprising between about 0.05% and 1% by weight of at least one ultraviolet absorber selected from the group consisting of homosalate, octisalate, octocrylene, and oxybenzone; and between about 0.05% and 1% by weight ensulizole.

14. The ophthalmic solution of claim 12 further comprising between about 0.01 and 2.66 µM riboflavin-5-sodium phosphate.

15. The ophthalmic solution of claim 1 wherein the solution consists essentially of the ultraviolet-A absorber, the ultraviolet-B absorber, at least one preservative; at least one surfactant or emulsifier, at least one buffering agent, a viscosity building agent, an HEV filter compound, and at least one additional chromophore for absorbing ultraviolet radiation.

16. The ophthalmic solution of claim 12 wherein the solution consists essentially of the avobenzone, the methoxycinnamate, the polysorbate 80, propylene glycol, methyl paraben, propyl paraben, an HEV filter compound and optionally at least one buffering agent.

* * * * *